(12) United States Patent
Wang et al.

(10) Patent No.: US 9,176,053 B1
(45) Date of Patent: Nov. 3, 2015

(54) METHOD FOR DETECTING AN ETCHING RESIDUE

(71) Applicants: BOE TECHNOLOGY GROUP CO., LTD., Beijing (CN); BEIJING BOE DISPLAY TECHNOLOGY CO., LTD., Beijing (CN)

(72) Inventors: Linlin Wang, Beijing (CN); Xi Chen, Beijing (CN); Shoukun Wang, Beijing (CN); Jianfeng Yuan, Beijing (CN)

(73) Assignees: BOE TECHNOLOGY GROUP CO., LTD (CN); BEIJING BOE DISPLAY TECHNOLOGY CO., LTD. (CN)

( * ) Notice: Subject to any disclaimer, the term of this patent is extended or adjusted under 35 U.S.C. 154(b) by 94 days.

(21) Appl. No.: 14/349,008

(22) PCT Filed: Aug. 9, 2013

(86) PCT No.: PCT/CN2013/081147
§ 371 (c)(1),
(2) Date: Apr. 1, 2014

(87) PCT Pub. No.: WO2014/198082
PCT Pub. Date: Dec. 18, 2014

(30) Foreign Application Priority Data

Jun. 13, 2013 (CN) .......................... 2013 1 0233393

(51) Int. Cl.
*G01N 21/94* (2006.01)
*G01N 21/3563* (2014.01)
(Continued)

(52) U.S. Cl.
CPC ............ *G01N 21/3563* (2013.01); *G01N 21/94* (2013.01); *G01N 21/956* (2013.01); *G01N 2021/3568* (2013.01); *G01N 2021/3595* (2013.01); *G01N 2201/061* (2013.01)

(58) Field of Classification Search
CPC .................... G01N 2021/3595; G01N 21/956; G03F 7/42; H01L 21/311

USPC ....................................................... 250/339.08
See application file for complete search history.

(56) References Cited

U.S. PATENT DOCUMENTS 5,903,006 A * 5/1999 Kiuchi et al. ............ 250/339.12
6,452,671 B1 9/2002 Uda et al.
(Continued)

FOREIGN PATENT DOCUMENTS

CN 1596368 A 3/2006
CN 102073227 A 5/2011
(Continued)

OTHER PUBLICATIONS

Chinese Office Action Dated May 28, 2015, Application No. 201310233393.6, 6 Pages.
(Continued)

*Primary Examiner* — Marcus Taningco
(74) *Attorney, Agent, or Firm* — Brooks Kushman P.C.

(57) ABSTRACT

The embodiments of the present invention provide a method for detecting an etching residue and relate to the field of display technologies, with the purpose of detecting an etching residue so as to improve product yield. The method comprises: fitting the boundary of a pattern in a position to be detected by film color difference, and positioning the pattern in a position to be detected, thereby acquiring the pattern in a position to be detected; testing an infrared spectrum of the pattern in a position to be detected, and obtaining an infrared spectrogram; determining whether the residue exists according to the infrared spectrogram. The method of the invention may be applicable for the detection of an etching residue during the process of preparing an array substrate or a cell substrate.

14 Claims, 10 Drawing Sheets

(51) Int. Cl.
*G01N 21/956* (2006.01)
*G01N 21/35* (2014.01)

(56) References Cited

U.S. PATENT DOCUMENTS

| | | | |
|---|---|---|---|
| 7,525,651 | B2 | 4/2009 | Uda et al. |
| 2003/0235997 | A1* | 12/2003 | Lee et al. .................. 438/745 |
| 2004/0168709 | A1* | 9/2004 | Drumm et al. ................ 134/18 |
| 2013/0157463 | A1* | 6/2013 | Goldfarb et al. ............. 438/689 |

FOREIGN PATENT DOCUMENTS

| | | |
|---|---|---|
| CN | 102354665 A | 2/2012 |
| CN | 102566327 A | 7/2012 |
| JP | 2001141657 A | 5/2001 |

OTHER PUBLICATIONS

PCT International Search Report and Written Opinion Dated Mar. 20, 2014, Application No. PCT/CN2013/081147, 12 Pages.

* cited by examiner

METHOD FOR DETECTING AN ETCHING RESIDUE

CROSS-REFERENCE TO RELATED APPLICATION

This application is the U.S. national phase of PCT Application No. PCT/CN2013/081147 filed on Aug. 9, 2013, which claims priority to Chinese Patent Application No. 201310233393.6 filed on Jun. 13, 2013, the disclosures of which are incorporated in their entirety by reference herein.

BACKGROUND OF THE INVENTION

1. Field of the Invention

The present invention relates to the field of display technologies, and in particular, to a method for detecting an etching residue.

2. Description of the Prior Art

During the process of producing an array substrate and a cell substrate, a patterning process is an indispensable step. Generally, the patterning process includes coating of photoresist, exposing, developing and etching. During an etching process, poor etch uniformity will often cause a problem of etching residues, wherein the etching residues refer to some residues existing after the patterning process. In other word, the film layer which should be fully removed is not totally removed.

For example, for a bottom gate-type array substrate, the production process may include: forming a gate, a gate insulating layer, an active layer, a source electrode and a drain electrode, and a protective layer and a pixel electrode in turn on a substrate, wherein the active layer may include an amorphous silicon layer and an n+ amorphous silicon layer, and the pixel electrode is connected with the drain by a via hole provided on the protective layer.

When forming the n+ amorphous silicon layer, the n+ amorphous silicon corresponding to the gap between the source electrode and the drain electrode must be fully etched. However, there usually exists a phenomenon that the n+ amorphous silicon is not fully etched after the etching process, which will cause a structure change of the final array substrate produced, thereby producing degraded products.

Additionally, when forming the via hole on the protective layer, the material of the protective layer at the via hole, such as silicon nitride, also must be fully etched. However, there usually also exists a phenomenon that the material of the protective layer at the via hole is not etched fully after the etching process, which will causes a result that the pixel electrode and the drain cannot be connected via the via hole, thereby producing degraded products.

SUMMARY OF THE INVENTION

Embodiments of the invention provide a method for detecting an etching residue, by which the etching residue may be detected, and thereby product yield is improved.

In order to achieve the above-mentioned aim, the embodiments of the invention employs the following technical solutions:

the method for detecting an etching residue, comprising:
fitting a boundary of a pattern in a position to be detected by color difference of film layers, and positioning the pattern in the position to be detected, and acquiring the pattern in the position to be detected;

testing the pattern in the position to be detected by an infrared spectroscopy, and obtaining an infrared spectrogram; and
determining whether there exists the residue according to the infrared spectrogram.

Optionally, said determining whether there exists the residue according to the infrared spectrogram comprises:
determining whether there exists a characteristic peak that characterizes a functional group or a chemical bond of the residue;
if there exists the characteristic peak, there exists the residue in the position to be detected; if there exists no characteristic peak, there exists no residue in the position to be detected.

Optionally, said testing the pattern in the position to be detected by the infrared spectroscopy comprises:
testing the pattern in the position to be detected by the infrared spectroscopy using a Fourier transform infrared spectrometer.

Further optionally, said method further comprises:
limiting an incident light of the Fourier transform infrared spectrometer to the position to be detected by providing a diaphragm corresponding to the pattern in the position to be detected, before testing the pattern in the position to be detected by the infrared spectroscopy and obtaining the infrared spectrogram, and after acquiring the pattern in the position to be detected.

Moreover, a part of the diaphragm through which a light transmits has the same shape with that of the pattern in the position to be detected, and has an area of less than or equal to that of the pattern in the position to be detected.

Optionally, the diaphragm is provided in the Fourier transform infrared spectrometer or on a side of the Fourier transforms infrared spectrometer through which a light exits.

Optionally, where a metal layer is provided directly under the position to be detected, said testing the pattern in the position to be detected by the infrared spectroscopy using the Fourier transform infrared spectrometer comprises: testing the pattern in the position to be detected by the infrared spectroscopy using a reflection-mode of the Fourier transform infrared spectrometer.

One embodiment of the invention provides a method for detecting an etching residue, which comprises acquiring the pattern in the position to be detected, testing the pattern in the position to be detected by an infrared spectroscopy and obtaining an infrared spectrogram, and determining whether there exists the residue according to the infrared spectrogram. Wherein, determining whether there exists the residue can make use of determining whether there exists the characteristic peak characterizing the functional group or the chemical bond of the residue. Therefore, the object of detecting the etching residue may be realized, and thereby product yield may be improved.

BRIEF DESCRIPTION OF THE DRAWINGS

In order to more clearly illustrates the technical solutions of the embodiments of the invention or the prior art, the drawings required in the specification of the embodiments or the prior art will be described briefly as follow. Apparently, the following drawings are only some embodiments of the invention, and one of ordinary skills in the art may also obtain other drawings according to these drawings without creative work.

REFERENCE NUMBERS

10: Substrate, 20: Gate electrode, 30: Gate Insulating Layer, 40: Active Layer, 401: Amorphous Silicon Layer, 402: n+Amorphous Silicon Layer, 402a: n+Amorphous Silicon Residue, 501: Source electrode, 502: Drain electrode, 60: Protective Layer, 601: Via hole, 601a: Silicon Nitride Residue, 100: Diaphragm, 100a: U-shaped part through which a light transmit, 100b: O-shaped part through which a light transmit, 200: Fourier Transform Infrared Spectrometer.

DETAILED DESCRIPTION OF THE PREFERRED EMBODIMENTS

Technical solutions of embodiments of the invention will be described clearly and fully as follow in conjunction with the drawings in the embodiments of the invention; and apparently, the embodiments described are only a part of embodiments of the invention, rather than the whole embodiments. Other embodiments made by one of ordinary skills in the art based on the embodiments of the invention without creative work all fall into the protection scope of the invention.

Figure 1:
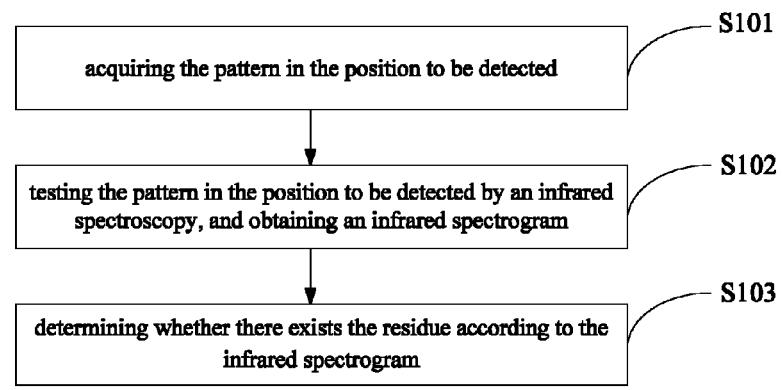
FIG. 1 is a schematic diagram showing processes for detecting an etching residue according to one embodiment of the invention.

One embodiment of the invention provides a method for detecting an etching residue comprising S101-S103, as shown in FIG. 1.

Figure 2:
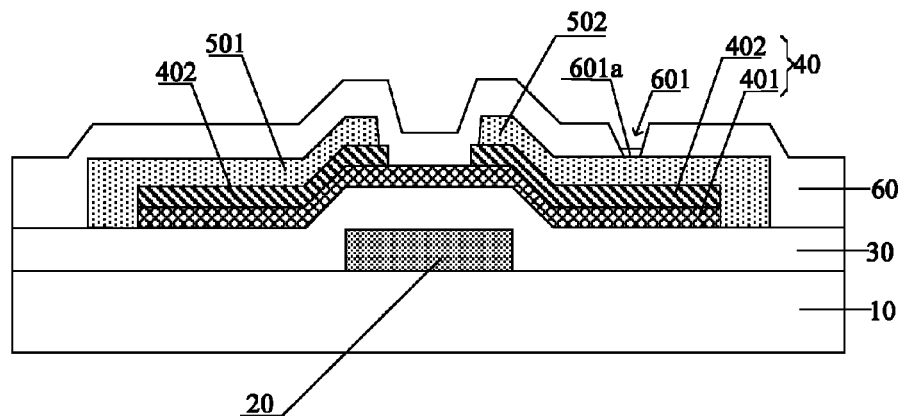
FIG. 2 is a structural representation showing the residual silicon nitride around a via hole on a protective layer of an array substrate according to one embodiment of the invention.
Figure 3:
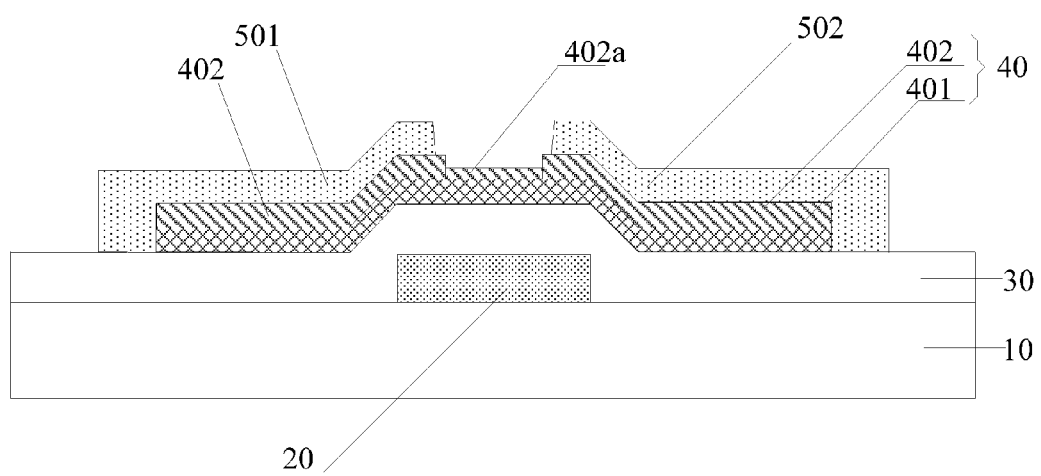
FIG. 3 is a structural representation showing the residual n+ amorphous silicon on an active layer corresponding to a gap between a source and a drain of an array substrate according to one embodiment of the invention.

S101: acquiring a pattern in a position to be detected.

Wherein this step may specifically comprise fitting a boundary of a pattern in a position to be detected by color difference of film layers, and positioning the pattern in the position to be detected, and acquiring the pattern in the position to be detected.

Wherein the term of "fitting" refers to identifying a pattern in a position to be detected by thin layer chromatography so as to form a diaphragm.

Wherein the position to be detected that is mentioned in all the embodiments of the invention refers to a position where the residues, which must be etched, may be exist after etching. For example, as shown in FIG. 2, the residue may be materials of protective layer, such as silicon nitride residue 601a during a via hole 601 via which a drain electrode 502 and a pixel electrode (not shown) is formed by etching on a protective layer 60 in manufacturing of a bottom gate-type array substrate. In another example, as shown in FIG. 3, the etching residue may be the n+ amorphous silicon residue 402a and the like on an active layer 40 corresponding to a gap between a source electrode 501 and a drain electrode 502 after the source electrode 501 and the drain electrode 502 are formed in manufacturing of a bottom gate-type array substrate, wherein the active layer 40 includes an amorphous silicon layer 401 and an n+ amorphous silicon layer 402.

Here, it should be noted that, the bottom gate-type array substrate in all the embodiments and drawings of the invention comprise, from the bottom up, a substrate 10, a gate electrode 20 provided on the substrate, a gate insulating layer 30, a semiconductor active layer 40, a source-drain metal layer including a source electrode 501 and a drain electrode 502, and a protective layer. Wherein, the active layer 40 includes an amorphous silicon layer 401 and an n+ amorphous silicon layer 402; and a thin-film transistor of the array substrate consist of the gate electrode 20, the gate insulating layer 30, the semiconductor active layer 40, the source electrode 501 and the drain electrode 502. The pixel electrode is not shown in the drawings.

Correspondingly, the pattern in the position needed to be detected may include pattern under the via hole, or the pattern under the position corresponding to the gap between the source electrode and the drain electrode.

S102: testing the pattern in the position to be detected by an infrared spectroscopy, and obtaining an infrared spectrogram.

Wherein, this step may specifically include: testing the pattern in the position to be detected by the infrared spectroscopy using a Fourier transform infrared spectrometer and obtaining the infrared spectrogram.

The Fourier transform infrared spectrometer (FTIR Spectrometer, for short) is an instrument that analyzes molecular structure and composition of matter according to the absorption characteristic of matter for infrared radiations having different wavelengths. The principle thereof is as follows: when matter is subjected to infrared radiations with a consecutively variable frequency, molecules of which the matter consist produce vibration movement and rotation movement due to absorbing the radiations of certain frequencies, which causes variation of the dipole moment and a energy level produced by vibration and rotation of molecules transits from ground state to excited state, and thereby a molecular absorption spectrum referred to as infrared spectrum is produced.

In order to limit an incident light from the Fourier transform infrared spectrometer to the position to be detected, preferably, before S102 and after S101, the method further comprises limiting the incident light of the Fourier transform infrared spectrometer to the position to be detected by providing a diaphragm corresponding to the pattern in the position to be detected.

In this way, it can be guaranteed that the incident light only irradiates on the pattern in the position to be detected to avoid the inaccuracy of test results caused by irradiation of the incident light on a position not to be detected.

In practical test, in order to avoid that the incident light from the Fourier transform infrared spectrometer irradiates on other film layers around the pattern in the position to be detected and interferes with test result of infrared spectrogram, preferably, a part of the diaphragm through which a light transmits has the same shape with that of the pattern in the position to be detected, and has an area of less than or equal to that of the pattern in the position to be detected. Wherein, the part of the diaphragm through which a light transmits has preferably an area of slightly less than that of the pattern in the position to be detected.

Here, it should be noted that, in the test by the infrared spectroscopy, the position of the part of the diaphragm through which a light transmits must fully correspond to the pattern in the position to be detected. Moreover, the diaphragm may be provided in the Fourier transform infrared spectrometer, or provided independently, which is not limited here.

Additionally, because the array substrate includes a gate metal layer and a source-drain metal layer through which a light cannot transmit, where a metal layer is provided directly under the position to be detected, the pattern in the position to be detected is tested by the infrared spectroscopy using a reflection-mode of the Fourier transform infrared spectrometer.

Wherein by taking a gate metal layer provided directly under the position to be detected as an example, the principle of testing the pattern at the position to be detected by the infrared spectroscopy using a reflection-mode of the Fourier transform infrared spectrometer and obtaining the infrared spectrogram lies in:
when the incident light from the Fourier transform infrared spectrometer irradiates on the pattern corresponding to the gap between the source electrode 501 and the drain electrode 502, the infrared light passes through the film layer having possibly an residua, which is n+ amorphous silicon residue 402a here, and then reaches the metal layer of the gate electrode 20 under the amorphous silicon layer 401 after passing through the amorphous silicon layer 401, and the light is finally reflected by the metal layer. In this process, each of film layers absorb a part of infrared lights with a certain frequency, and signals of the reflected light are collected, detected and converted into the corresponding infrared spectrogram by the Fourier transform infrared spectrometer.

Additionally, in one embodiment of the invention, the infrared spectrogram is obtained by a Fourier transform infrared spectrometer, and whether there exists an etching residue is determined mainly utilizing the character of the infrared spectrum, i.e., having a characteristic peak which will appear in the position corresponding to the wavelength or the wave number of the absorbed light in the infrared spectrogram. Wherein, each of characteristic peaks in the infrared spectrogram represents specific vibration mode of a certain functional group or a chemical bond, and each of characteristic peaks corresponds to a specific wavelength or a wave number on the infrared spectrogram.

S103: determining whether the residue exists according to the infrared spectrogram.

wherein, this step may include specially: according to the infrared spectrogram, determining whether there exists a characteristic peak corresponding to the wave number of the functional group or chemical bond by which the residue is characterized; if there exists the characteristic peak, there exists the residue in the position to be detected; if there exists no characteristic peak, there exists no residue in the position to be detected.

One embodiment of the invention provides a method for detecting an etching residue, which comprises acquiring the pattern in the position to be detected, testing the pattern in the position to be detected by an infrared spectroscopy and obtaining an infrared spectrogram, and determining whether there exists the residue according to the infrared spectrogram. Wherein, determining whether there exists the residue can make use of determining whether there exists the characteristic peak characterizing the functional group or the chemical bond of the residue. Therefore, the object of detecting the etching residue may be realized, and thereby product yield may be improved.

Two specific examples will be given to describe the method for detecting the etching residue in detail.

By taking a bottom gate-type array substrate as an example, the method for producing the same comprises: forming a gate electrode, a gate insulating layer, an active layer, a source-drain metal layer, a protective layer and a pixel electrode on the protective layer in turn on a substrate, wherein the active layer includes an amorphous silicon layer and an n+ amorphous silicon layer, the source-drain metal layer includes a via hole, and the pixel electrode is electrically connected with the drain electrode via the via hole formed on the protective layer. A thin-film transistor of the array substrate consists of the gate, the gate insulating layer, the active layer, the source electrode and the drain electrode form.

Embodiment 1

Determining whether there exists a n+ amorphous silicon residue in the active layer corresponding to a gap between a source electrode and the drain electrode after forming the source electrode and the drain electrode.

The method for detecting the etching residue comprises Steps S201-S204.

S201: fitting the pattern corresponding to the gap between the source electrode 501 and the drain electrode 502 of the source-drain metal layer by color difference of between the source-drain metal layer and the active layer 40, and positioning the pattern and obtaining the pattern.

Figure 4A:
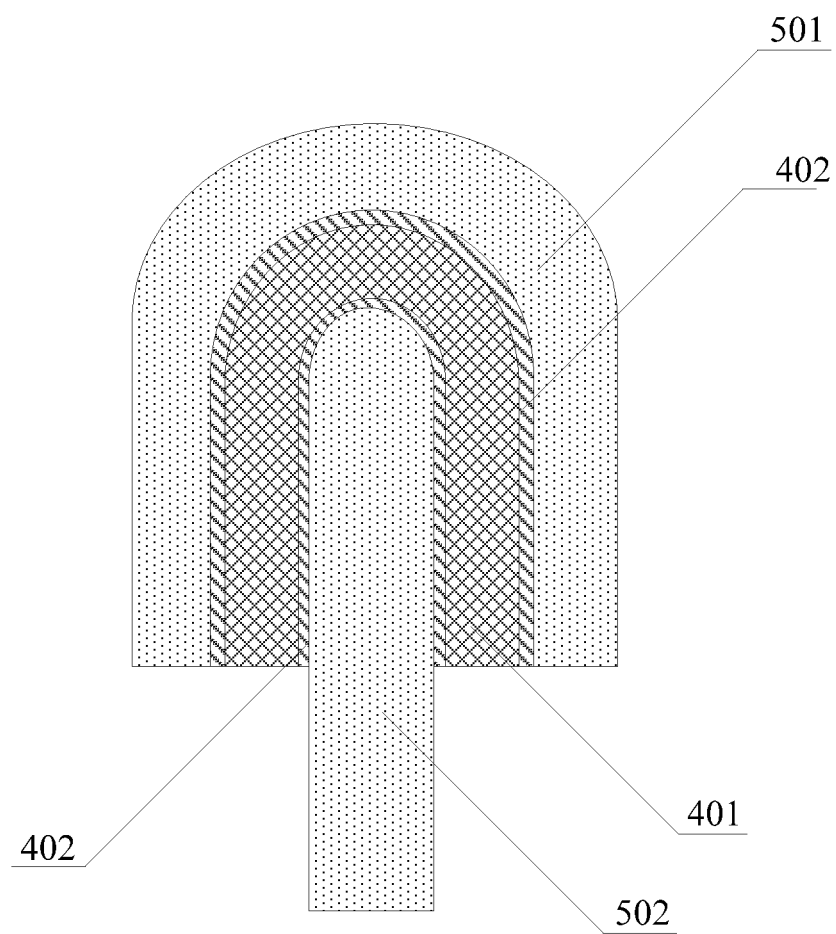
FIG. 4a is a schematic top view of a thin-film transistor array substrate showing no n+ amorphous silicon residue exists in a pattern corresponding to a gap between a source and a drain according to Embodiment 1 of the invention.
Figure 5A:
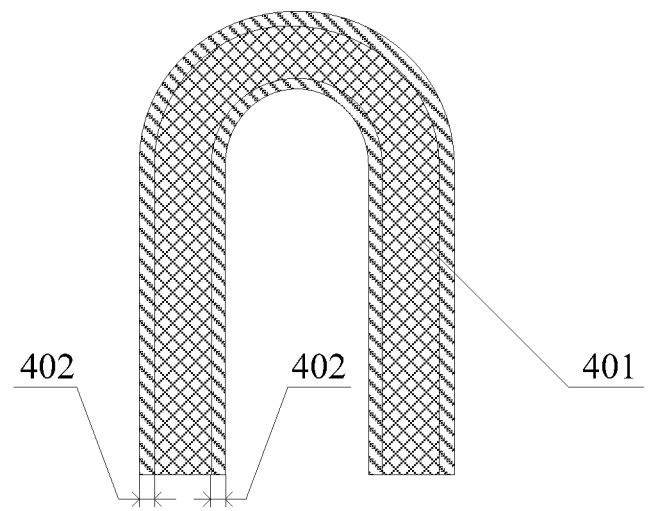
FIG. 5a is a schematic top view showing no n+ amorphous silicon residue exists in a pattern corresponding to a gap between a source and a drain according to Embodiment 1 of the invention.

For example, as shown in FIG. 4a, when no n+ amorphous silicon residue exists in the pattern corresponding to the gap between the source electrode 501 and the drain electrode 502, the pattern corresponding to the gap between the source electrode 501 and the drain electrode 502 only includes a part of a pattern of the active layer, i.e., a part of a pattern of the amorphous silicon layer 401 and the n+ amorphous silicon layer 402, as shown in FIG. 5a.

Figure 4B:
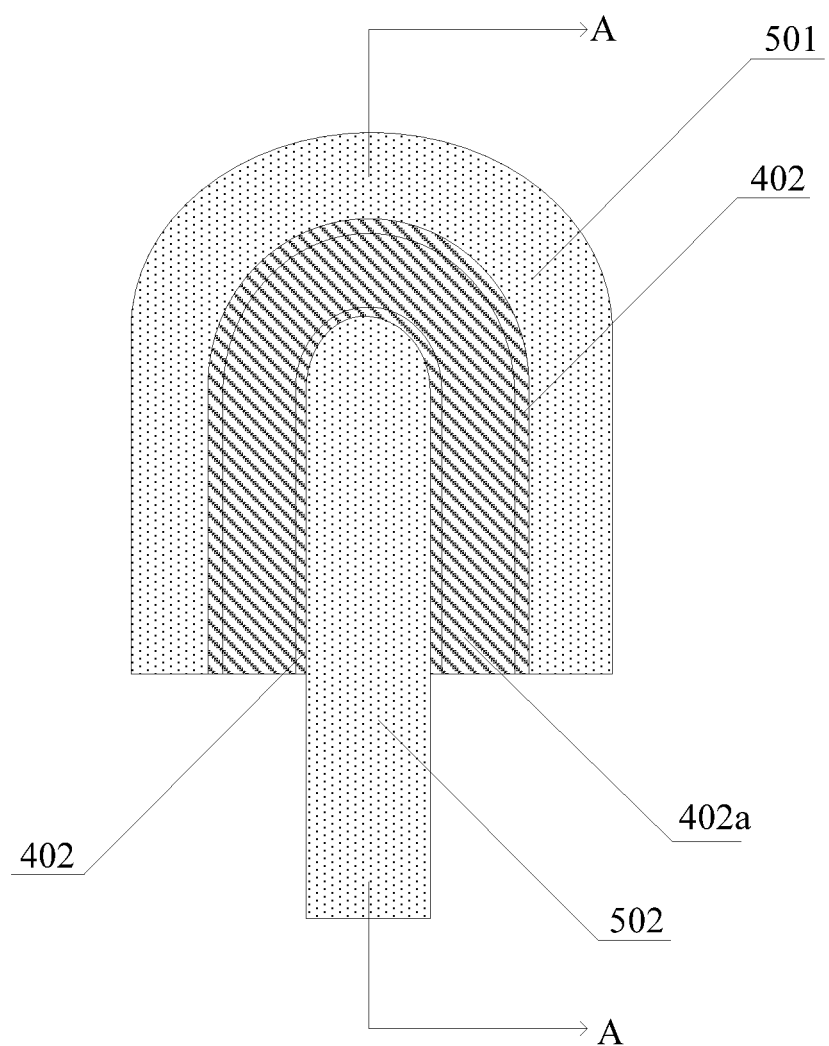
FIG. 4b is a schematic top view of a thin-film transistor array substrate showing n+ amorphous silicon residue exists in a pattern corresponding to a gap between a source and a drain according to Embodiment 1 of the invention.
Figure 5B:
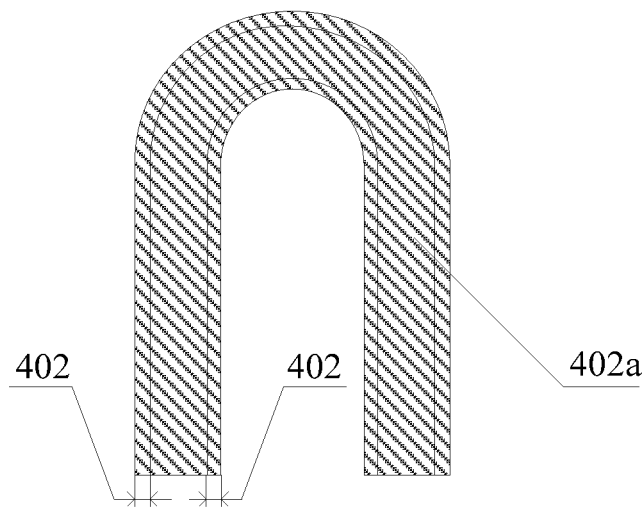
FIG. 5b is a schematic top view showing n+ amorphous silicon residue exists at a pattern corresponding to a gap between a source and a drain according to Embodiment 1 of the invention.

For example, as shown in FIG. 4b, when n+ amorphous silicon residue 402a exists in the pattern corresponding to the gap between the source electrode 501 and the drain electrode 502, the pattern corresponding to the gap between the source electrode 501 and the drain electrode 502 includes not only a part of the pattern of the active layer, but also the n+ amorphous silicon residue 402a, as shown in FIG. 5b. Wherein, FIG. 5b is a top view, only a part of the pattern of the n+ amorphous silicon layer 402 of the active layer can be seen in FIG. 5b.

As shown in FIG. 4 or 5, the active layer and the source-drain metal layer are formed, as limited by patterning process, when detecting in a position which is above the gap between the source electrode 501 and the drain electrode 502, the n+ amorphous silicon layer 402 of the active layer includes a pattern of n+ amorphous silicon layer 402 with a width of about 0.4 µm under the relative boundary of the source electrode 501 and the drain electrode 502, thus during practical testing, even if there exists no n+ amorphous silicon residue 402a in the pattern corresponding to the gap between the source electrode 501 and the drain electrode 502. Thus, the part of the pattern of the n+ amorphous silicon layer 402 with a width of about 0.4 µm should be excluded in actual test.

It should be noted that fitting method by color difference of film layers is not limited to all the embodiments of the invention.

S202: according to the pattern corresponding to the gap between the source electrode 501 and the drain electrode 502, limiting the incident light from the Fourier transform infrared spectrometer to the pattern by providing a diaphragm including a part which has a shape corresponding to a shape of the pattern through which a light transmits.

Figure 6:
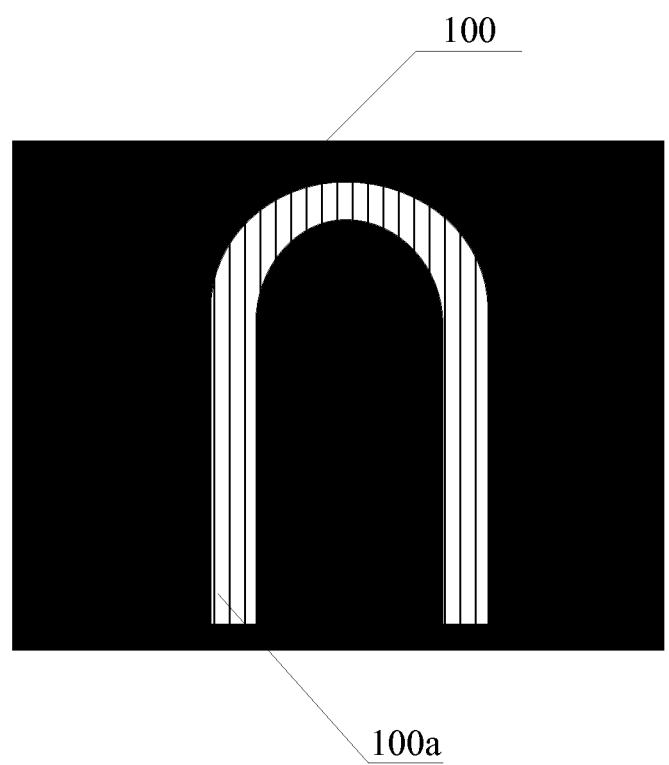
FIG. 6 is a schematic diagram showing a diaphragm comprising a U-shaped part through which a light transmit according to Embodiment 1 of the invention.

According to a shape of the pattern corresponding to the gap between the source electrode 501 and the drain electrode 502 as shown in FIG. 5a or 5b, for example, U-shaped, a diaphragm 100 including a part corresponding to the shape of the pattern through which a light transmits is provided, wherein the U-shaped part 100a of the diaphragm 100 through which a light transmits has a shape as shown in FIG. 6 and an area of slightly less than that of a part 401 shown in FIG. 5a or a part 402a shown in FIG. 5b. In other word, the area is slightly less than that by subtracting an area of the pattern of the n+ amorphous silicon layer 402 with the width mentioned above of about 0.4 µm from an area of the pattern corresponding to the gap between the source electrode 501 and the drain electrode 502 as shown in FIG. 5a or 5b.

S203: testing the pattern corresponding to the gap between the source electrode 501 and the drain electrode 502 by the infrared spectroscopy using a Fourier transform infrared spectrometer, and obtaining an infrared spectrogram.

Figure 7:
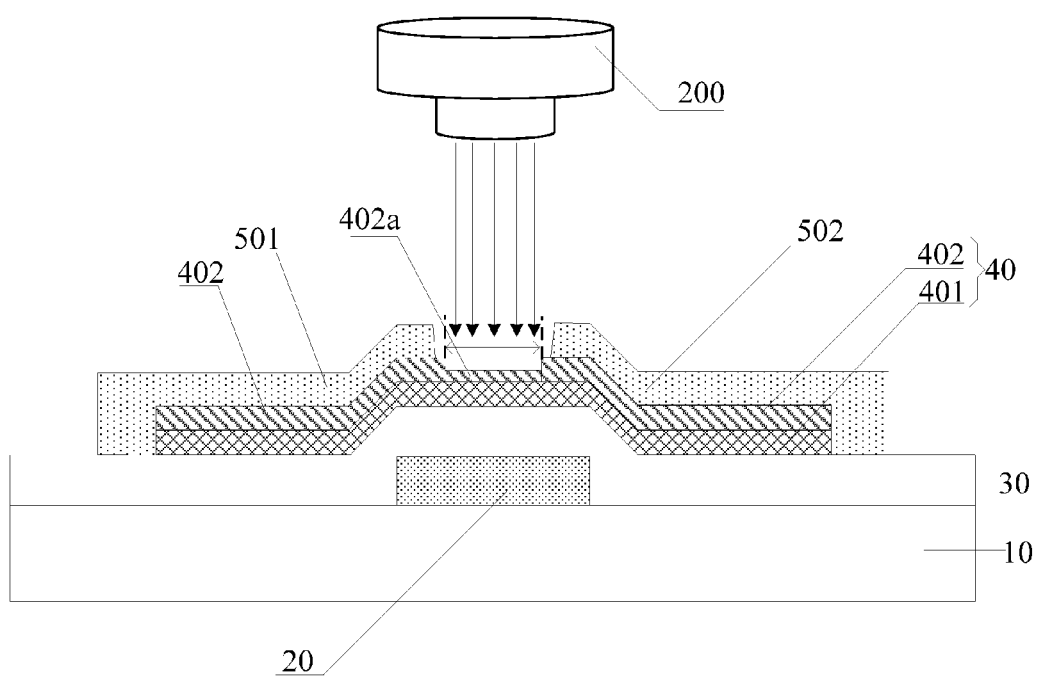
FIG. 7 is a schematic diagram showing processes of carrying out an infrared spectrum test using a Fourier transform infrared spectrometer comprising the U-shaped part through which a light transmit according to Embodiment 1 of the invention.

In this step, as shown in FIG. 7, the Fourier transform infrared spectrometer 200 comprising a diaphragm 100 (not shown in FIG. 7) including the U-shaped part 100a through which a light transmits may be employed, so that the incident lights from the Fourier transform infrared spectrometer are totally irradiated on the pattern corresponding to the gap between the source electrode 501 and the drain electrode 502. Additionally, because a gate 20 exists under the active layer and material of the gate 20 is a metal which can reflect lights, a reflection-mode of the Fourier transform infrared spectrometer is employed to test the pattern corresponding to the gap between the source electrode 501 and the drain electrode 502 by an infrared spectroscopy, so that the infrared spectrogram including information of various functional groups or chemical bonds is obtained.

Wherein, FIG. 7a is a sectional view of each of layers of the array substrate which is sectioned along the direction A-A in FIG. 4b, and FIG. 7 is only a schematic view containing the n+ amorphous silicon residue 402a.

S204: determining whether there exists a characteristic peak of a chemical bond characterizing the n+ amorphous silicon according to the infrared spectrogram.

In this embodiment, because the n+ amorphous silicon includes a P—H bond, it may determine whether there exists a characteristic peak corresponding to the wave numbers of the P—H bond, i.e., in or near the range of 2265-2455 cm$^{-1}$. If there exists no characteristic peak, it may be determined that no n+ amorphous silicon residue exists in the pattern corresponding to the gap between the source electrode 501 and the drain electrode 502; if there exists a characteristic peak, it may be determined that n+ amorphous silicon residue exists in the pattern corresponding to the gap between the source electrode 501 and the drain electrode 502.

Additionally, a residual quantity of n+ amorphous silicon may be measured according to intensity and a peak area of the characteristic peak corresponding to the P—H bond.

Embodiment 2

Determining whether there exists an residue of silicon nitride in a via hole after forming a protective layer (for example, with a material of silicon nitride)

The method for detecting an etching residue includes steps S301-S303.

S301: fitting the boundary of a via hole 601 on the protective layer 60 by color difference between the source-drain metal layer and the protective layer 60, positioning the via hole 601, and obtaining the pattern under the via hole 601.

Figure 8A:
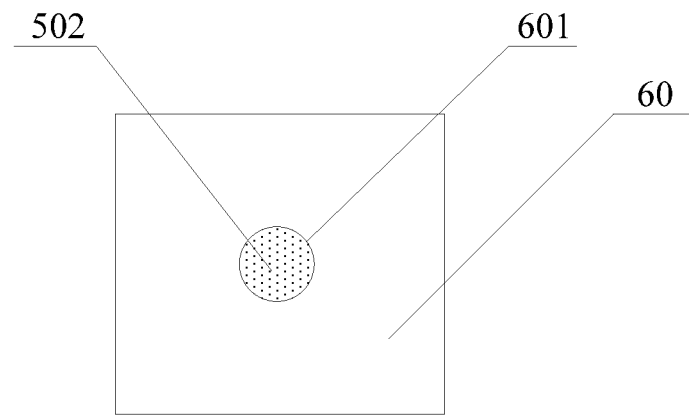
FIG. 8a is a schematic top view showing no silicon nitride residue exists in a pattern under a via hole according to Embodiment 2 of the invention.

For example, as shown in FIG. 8a, when no silicon nitride residue exists in the via hole 601, the pattern under the via hole 601 is a part of the pattern of the drain electrode 502 of the source-drain metal layer.

Figure 8B:
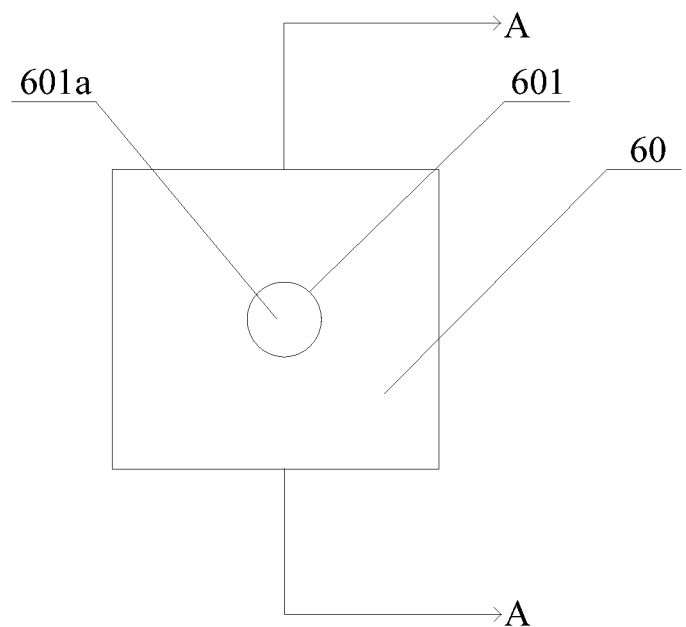
FIG. 8b is a schematic top view showing silicon nitride residue exists at a pattern under a via hole according to Embodiment 2 of the invention.

For example, as shown in FIG. 8b, when silicon nitride residue 601a exists in the via hole 601, the pattern under the via hole 601 is the pattern of the residue of silicon nitride 601a.

Here, when the residue of silicon nitride 601a exists in the via hole 601, because it is the residue of silicon nitride after etching, thickness of the residue is small. The boundary of the via hole may also be fitted by color difference between the source-drain metal layer and the protective layer.

S302: limiting the incident light from the Fourier transform infrared spectrometer to the pattern under the via hole 601 by providing a diaphragm including a part corresponding to a shape of the via hole 601 through which a light transmits, according to the pattern under the via hole 601.

Figure 9:
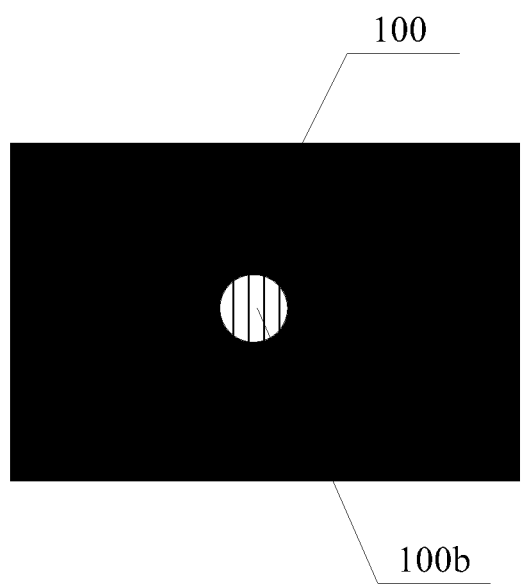
FIG. 9 is a schematic diagram showing a diaphragm comprising an O-shaped part through which a light transmit according to Embodiment 2 of the invention.

According to the shape of the pattern under the via hole 601 shown in FIG. 8a or FIG. 8b, for example, O-shaped, a diaphragm 100 including a part corresponding to the shape of the via hole 601 through which a light transmits is provided, wherein the O-shaped part 100b of the diaphragm 100 through which a light transmits has a shape as shown in FIG. 9 and the area of slightly less than that of the pattern under the via hole 601 as shown in FIG. 8a or FIG. 8b.

During etching, a surface area of the via hole 601 away from the source-drain metal layer on the protective layer 60 is larger than that of the via hole 601 near the source-drain metal layer. The area of the pattern under the via hole 601 referred to here is the surface area of the via hole 601 near the source-drain metal layer.

S303: testing the pattern under the via hole 601 by the infrared spectroscopy using the Fourier transform infrared spectrometer.

Figure 10:
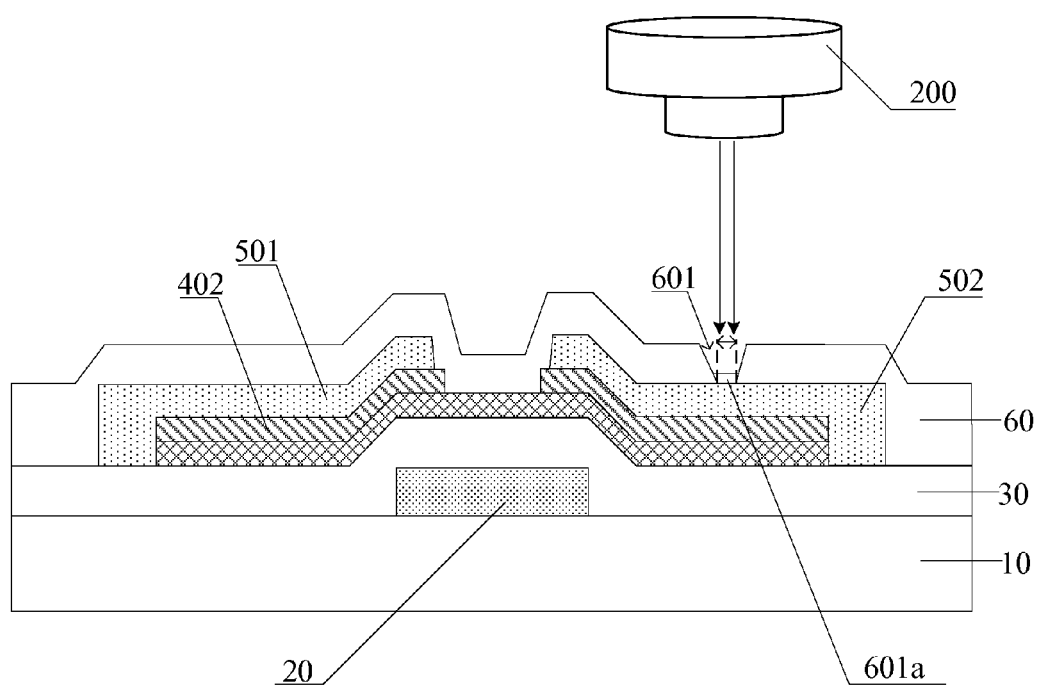
FIG. 10 is a schematic diagram showing processed of carrying out an infrared spectrum test using a Fourier transform infrared spectrometer comprising an O-shaped part through which a light transmit according to Embodiment 2 of the invention.

In this step, as shown in FIG. 10, a Fourier transform infrared spectrometer 200 may be employed, which comprises a diaphragm 100 (not shown in FIG. 10) including an O-shaped part 100b through which a light transmits, so that incident lights from the Fourier transform infrared spectrometer are totally irradiated on the pattern under the via hole 601. Additionally, because the drain electrode 502 is under the via hole 601 and material of the drain electrode is a metal which can reflect light, a reflection-mode of the Fourier transform infrared spectrometer is employed to test the pattern under the via hole 601 by the infrared spectroscopy, so that an infrared spectrogram including various functional groups or chemical bonds is obtained.

Wherein, FIG. 10 is a sectional view of each of layers of the array substrate which is sectioned along the direction A-A in FIG. 8b, and FIG. 10 is only a schematic view containing the residue of silicon nitride 601.

S304: determining whether there exists a characteristic peak characterizing a chemical bond of silicon nitride according to the infrared spectrogram.

In this embodiment, because silicon nitride includes three characteristic chemical bonds, i.e., Si—H, Si—N and N—H, it may be determined whether there exists such series of characteristic peaks corresponding to wave number of the Si—H, Si—N and N—H, near 2100 $cm^{-1}$, 840 $cm^{-1}$, 3350 $cm^{-1}$. If there exists no such series of characteristic peak, it may be determined that there exists no residue of silicon nitride in the via hole; if there exists such series of characteristic peak, it may be determined that there exists the residue of silicon nitride in the via hole.

The above only shows some preferred embodiments of the invention. It should be pointed out that, for one of ordinary skills in the art, various improvements and modifications may also be made without departing from the principle of the invention, and all these improvements and modifications should also be encompassed by the protection scope of the invention.

What is claimed is:

1. A method for detecting an etching residue, comprising:
    fitting a boundary of a pattern in a position to be detected by color difference of film layers, and positioning the pattern in the position to be detected, and acquiring the pattern in the position to be detected;
    testing the pattern in the position to be detected by an infrared spectroscopy, and obtaining an infrared spectrogram; and
    determining whether there exists the residue according to the infrared spectrogram.

2. The method for detecting an etching residue according to claim 1, wherein said determining whether there exists the residue according to the infrared spectrogram comprises:
    determining whether there exists a characteristic peak that characterizes a functional group or a chemical bond of the residue;
    if there exists the characteristic peak, there exists the residue in the position to be detected;
    if there exists no characteristic peak, there exists no residue in the position to be detected.

3. The method for detecting an etching residue according to claim 2, wherein said testing the pattern in the position to be detected by the infrared spectroscopy comprises: testing the pattern in the position to be detected by the infrared spectroscopy using a Fourier transform infrared spectrometer.

4. The method for detecting an etching residue according to claim 3, wherein said method further comprises:
    limiting an incident light of the Fourier transform infrared spectrometer to the position to be detected by providing a diaphragm corresponding to the pattern in the position to be detected, before testing the pattern in the position to be detected by the infrared spectroscopy and obtaining the infrared spectrogram, and after acquiring the pattern in the position to be detected.

5. The method for detecting an etching residue according to claim 4, wherein a part of the diaphragm through which a light transmits has the same shape with that of the pattern in the position to be detected, and has an area of less than or equal to that of the pattern in the position to be detected.

6. The method for detecting an etching residue according to claim 5, wherein the diaphragm is provided in the Fourier transform infrared spectrometer or on a side of the Fourier transform infrared spectrometer through which a light exits.

7. The method for detecting an etching residue according to claim 3, wherein a metal layer is provided directly under the position to be detected, and said testing the pattern in the position to be detected by the infrared spectroscopy using the Fourier transform infrared spectrometer comprises testing the pattern in the position to be detected by the infrared spectroscopy using a reflection-mode of the Fourier transform infrared spectrometer.

8. The method for detecting an etching residue according to claim 4, wherein the diaphragm is provided in the Fourier transform infrared spectrometer or on a side of the Fourier transform infrared spectrometer through which a light exits.

9. The method for detecting an etching residue according to claim 1, wherein said testing the pattern in the position to be detected by the infrared spectroscopy comprises:
    testing the pattern in the position to be detected by the infrared spectroscopy using a Fourier transform infrared spectrometer.

10. The method for detecting an etching residue according to claim 9, wherein said method further comprises:
    limiting an incident light of the Fourier transform infrared spectrometer to the position to be detected by providing a diaphragm corresponding to the pattern in the position to be detected, before testing the pattern in the position to be detected by the infrared spectroscopy and obtaining the infrared spectrogram, and after acquiring the pattern in the position to be detected.

11. The method for detecting an etching residue according to claim 10, wherein a part of the diaphragm through which a light transmits has the same shape with that of the pattern in the position to be detected, and has an area of less than or equal to that of the pattern in the position to be detected.

12. The method for detecting an etching residue according to claim 11, wherein the diaphragm is provided in the Fourier transform infrared spectrometer or on a side of the Fourier transform infrared spectrometer through which a light exits.

13. The method for detecting an etching residue according to claim 9, wherein a metal layer is provided directly under the position to be detected, and said testing the pattern in the position to be detected by the infrared spectroscopy using the Fourier transform infrared spectrometer comprises testing the pattern in the position to be detected by the infrared spectroscopy using a reflection-mode of the Fourier transform infrared spectrometer.

14. The method for detecting an etching residue according to claim 10, wherein the diaphragm is provided in the Fourier transform infrared spectrometer or on a side of the Fourier transform infrared spectrometer through which a light exits.

* * * * *

UNITED STATES PATENT AND TRADEMARK OFFICE
CERTIFICATE OF CORRECTION

| | | |
|---|---|---|
| PATENT NO. | : 9,176,053 B1 | Page 1 of 1 |
| APPLICATION NO. | : 14/349008 | |
| DATED | : November 3, 2015 | |
| INVENTOR(S) | : Linlin Wang et al. | |

It is certified that error appears in the above-identified patent and that said Letters Patent is hereby corrected as shown below:

Claims

Column 9, Line 52, Claim 3:

After "according to claim"
Delete "2" and
Insert -- 1 --.

Column 10, Line 9, Claim 6:

After "according to claim"
Delete "5" and
Insert -- 4 --.

Column 10, Line 22, Claim 8:

After "according to claim"
Delete "4" and
Insert -- 5 --.

Column 10, Line 26, Claim 9:

After "according to claim"
Delete "1" and
Insert -- 2 --.

Signed and Sealed this
Nineteenth Day of April, 2016

Michelle K. Lee
*Director of the United States Patent and Trademark Office*